United States Patent
Pope, Jr.

[11] Patent Number: 5,806,525
[45] Date of Patent: Sep. 15, 1998

[54] APPARATUS AND METHOD FOR IMPROVING NASAL BREATHING

[76] Inventor: Thaddeus Harris Pope, Jr., 71 Twin Oaks, Crawfordsville, Ind. 47933

[21] Appl. No.: 714,693

[22] Filed: Sep. 16, 1996

[51] Int. Cl.$^6$ ................................................. A61F 5/56
[52] U.S. Cl. ........................ 128/848; 128/858; 602/902; 606/204.45
[58] Field of Search .................................. 128/845, 846, 128/857, 858, 200.24, 204.12, 206.18, 207.18, 912, 848, DIG. 26; 606/191, 196, 199, 204.45; 602/54, 56, 58

[56] References Cited

U.S. PATENT DOCUMENTS

| | | | |
|---|---|---|---|
| 3,426,751 | 2/1969 | Radewan | 606/204.45 |
| 4,340,040 | 7/1982 | Straith | 606/204.45 |
| 5,022,389 | 6/1991 | Brennan | 606/204.45 |
| 5,533,499 | 7/1996 | Johnson . | |
| 5,533,503 | 7/1996 | Doubek et al. . | |
| 5,553,605 | 9/1996 | Muchin | 128/207.18 |

FOREIGN PATENT DOCUMENTS 79262  10/1962  France ............................. 606/204.45

OTHER PUBLICATIONS

Product Brochure for "Bridgemaster Nasal Splint," Manufactured by Merocel Surgical Products of Mystic, Connecticut—Copyright 1995.

Instruction set for "Breathe Right" Nasal Strips, Manufactured by CNS, Inc. of Chanhassen, Minnesota—Copyright 1995.

Primary Examiner—Michael A. Brown
Attorney, Agent, or Firm—Maginot, Addison & Moore

[57] ABSTRACT

An apparatus for opening nasal passages of a human head is disclosed, with the human head having a nose, a first cheek and a second cheek, and with the nose having a bridge portion, a first nasal wall and a second nasal wall. The apparatus includes a metallic biasing member having a length sufficient to span a distance from the first nasal wall to the second nasal wall across the bridge portion. The apparatus further includes a non-woven base, secured to the biasing member, having a length sufficient to span a distance from the first cheek to the second cheek across the nose. Additionally, the apparatus includes an adhesive material disposed on the baising member and the base for attaching the baising member and the base to the human head. Moreover, the apparatus includes a strippable liner positioned in contact with the adhesive material. A method of opening nasal passages of a human head is also disclosed.

28 Claims, 5 Drawing Sheets

APPARATUS AND METHOD FOR IMPROVING NASAL BREATHING

BACKGROUND OF THE INVENTION

The present invention relates generally to an apparatus and method for improving nasal breathing, and more particularly to an apparatus and method for opening nasal passages within a human head.

Many individuals have difficulty breathing through their nose. Such difficulties can be the result of anatomical anomalies within the nasal passages, illnesses, allergies, etc.

Such difficulties can be detrimental to an individual's ability to sleep well. In particular, the individual may awaken frequently during the night due to breathing difficulties or may snore excessively. Moreover, breathing difficulties may also be detrimental to an individual's athletic performance, wherein it is imperative to maintain a consistent flow of air through the nasal passages and into the lungs in order to oxygenate the blood flowing therein.

In an attempt to improve breathing through the nose, numerous medications have been developed. However, such medications can be expensive. Moreover, the user can experience side effects and, in some circumstances, the user can actually develop a dependency on the medications.

In addition, surgical techniques exist to improve nasal breathing. However, such techniques are invasive and may involve an extended post-operative recovery period, and moreover may be financially burdensome to a patient.

As a result, devices, known as nasal strips, have been created to improve breathing without the use of medications or surgical techniques. Nasal strips are affixed to the outside of the nose and exert outward forces on the nasal cartilages of the nose, thereby allowing the nasal passages to be pulled open. This enables enhanced air flow through the nasal passages, thereby allowing the user to breathe more efficiently.

However, known nasal strips do not provide adequate retaining forces. In particular, the outward forces exerted on the nasal cartilages by known nasal strips do not hold the nasal passages sufficiently open.

What is needed therefore, is an apparatus and method for holding the nasal passages of the nose more fully opened to allow enhanced breathing. Such an apparatus should use commonly available materials and have a relatively low manufacturing cost.

SUMMARY OF THE INVENTION

In accordance with one embodiment of the present invention, there is provided an apparatus for opening nasal passages of a human head having a nose, a first cheek and a second cheek, with the nose having a bridge portion, a first nasal wall and a second nasal wall. The apparatus includes a metallic biasing member having a length sufficient to span a distance from the first nasal wall to the second nasal wall across the bridge portion. The apparatus further includes a non-woven base, secured to the biasing member, having a length sufficient to span a distance from the first cheek to the second cheek across the nose. Moreover, the apparatus includes an adhesive material disposed on the baising member and the base for attaching the baising member and the base to the human head. Additionally, the apparatus includes a strippable liner positioned in contact with the adhesive material.

Pursuant to another embodiment of the present invention, there is provided an apparatus for opening nasal passages of a human head having a nose, a first cheek and a second cheek, with the nose having a bridge portion, a first nasal wall and a second nasal wall. The apparatus includes a biasing member having a length sufficient to span a distance from the first nasal wall to the second nasal wall across the bridge portion. Further, the apparatus includes a base, secured to the biasing member, having a length sufficient to span a distance from the first cheek to the second cheek across the nose. The apparatus additionally includes an adhesive material for attaching the biasing member and the base to the human head.

In accordance with yet another embodiment of the present invention, there is provided an apparatus for opening nasal passages of a human head having a nose, with the nose having a bridge portion, a first nasal wall, and a second nasal wall. The apparatus includes a metallic biasing member having a length sufficient to span a distance from the first nasal wall to the second nasal wall across the bridge portion, the biasing member further having a first nasal wall support portion and a second nasal wall support portion. The apparatus further includes an adhesive material disposed on (1) the first nasal wall support portion of the biasing member, and (2) the second nasal wall support portion of the biasing member.

In accordance with still another embodiment of the present invention, there is provided a method of opening nasal passages of a human head having a nose, a first cheek and a second cheek, with the nose having a bridge portion, a first nasal wall, and a second nasal wall. The method includes the steps of (1) providing a biasing member having a length sufficient to span a distance from the first nasal wall to the second nasal wall, (2) providing a base having a length sufficient to span a distance from the first cheek to the second cheek across the nose, and (3) attaching the biasing member and the base to the human head so that (i) the biasing member is juxtaposed to the first nasal wall, the second nasal wall, and the bridge portion, and (ii) the base is juxtaposed to the first cheek, the second cheek and the nose.

It is therefore an object of the present invention to provide a new and useful nasal strip.

It is further an object of the present invention to provide an improved nasal strip.

It is yet another object of the present invention to provide a new and useful method for improving nasal breathing.

It is moreover an object of the present invention to provide an improved method for improving nasal breathing.

It is further an object of the present invention to provide a nasal strip which is capable of holding the nasal passages of the nose more completely open relative known nasal strips.

It is yet another object of the present invention to provide a nasal strip which is relatively easy to manufacture.

The above and other objects, features, and advantages of the present invention will become apparent from the following description and the attached drawings.

DETAILED DESCRIPTION OF THE INVENTION

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 1:
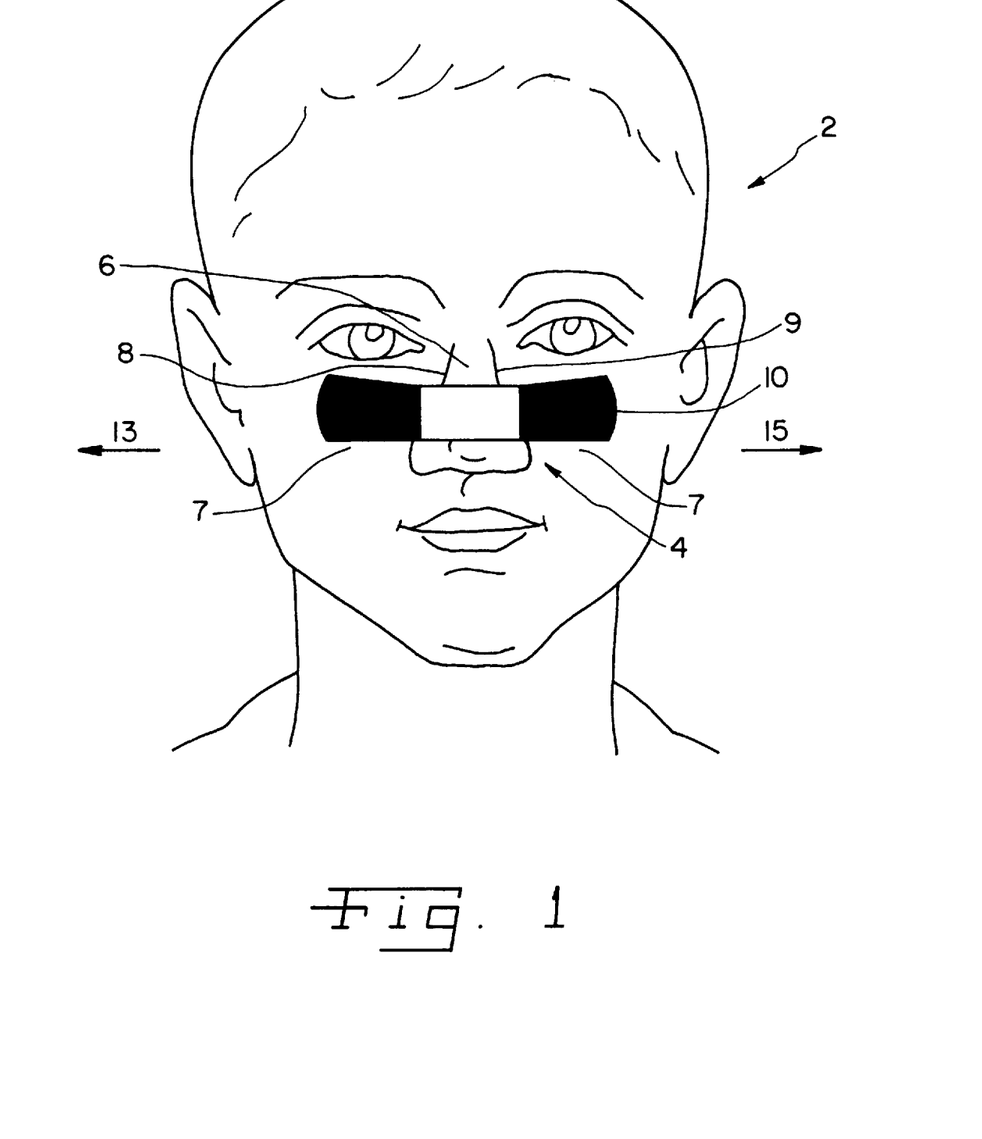
FIG. 1 is a front elevational view of a human head with a first embodiment of a nasal strip attached thereto which incorporates the features of the present invention therein.
Figure 2:
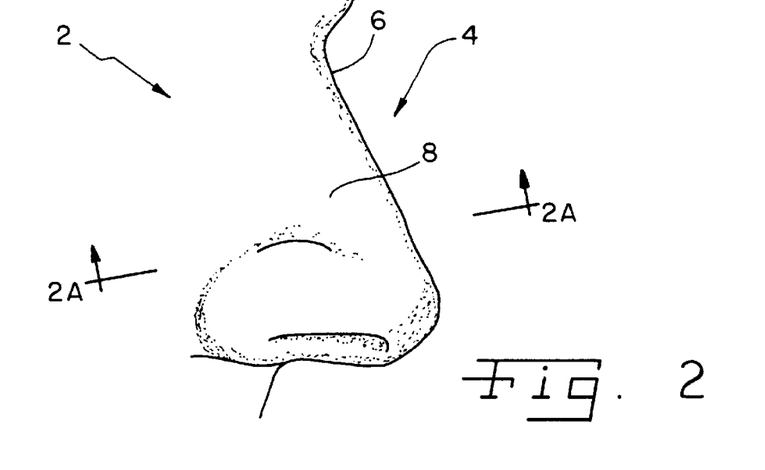
FIG. 2 is a fragmentary perspective view of the human head of FIG. 1 showing a nose.
Figure 2A:
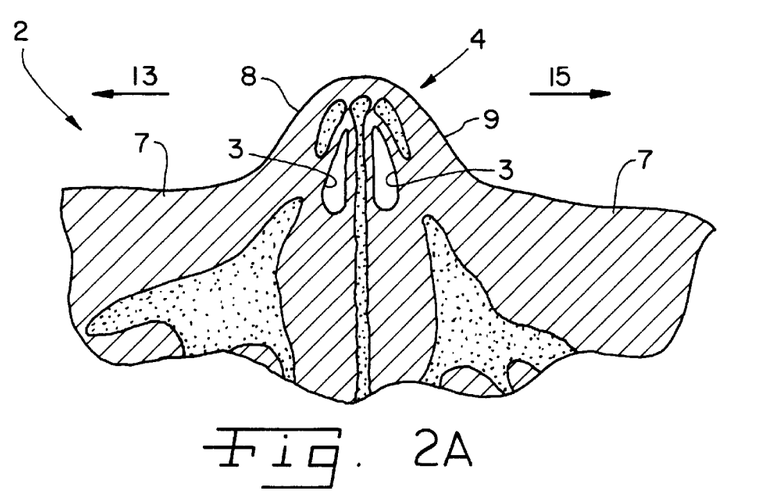
FIG. 2A is a cross sectional view of the nose of FIG. 2, taken along the lines 2A—2A of FIG. 2 as viewed in the direction of the arrows.
Figure 3:
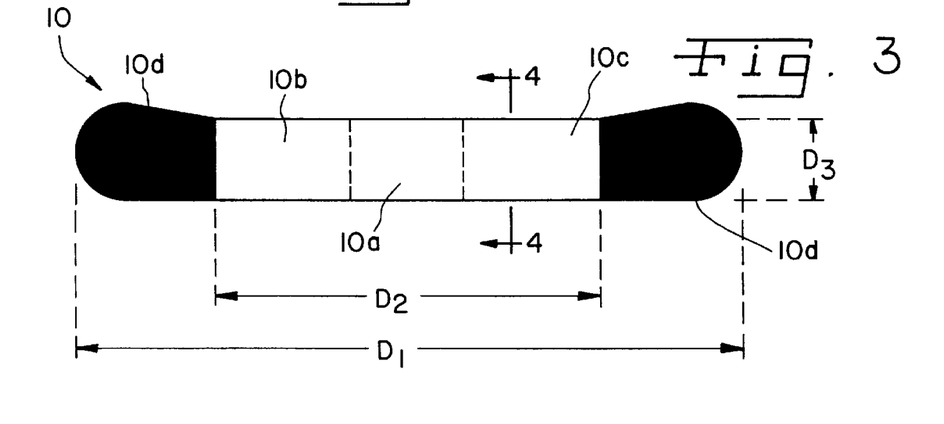
FIG. 3 is an elevational view of the nasal strip of FIG. 1 prior to attachment to the human head.

Referring now to FIGS. 1, 2, and 2A, there is shown a human head 2 including a nose 4. The nose 4 of FIG. 1 has a nasal strip 10 attached thereto which incorporates the features of the present invention therein. As shown in FIGS. 2 and 3, the nose 4 includes a pair of nasal passages 3, a bridge 6, a first nasal wall 8, and a second nasal wall 9. What is herein meant by the term "bridge" is the area of the nose including the anatomical structures known as the nasal bone (not shown), the septal cartilage (not shown), and the tissues and skin attached thereto. Moreover, what is herein meant by the term "nasal wall" is the area of the nose (contained within dashed lines in FIG. 2) including the anatomical structures known as the upper lateral cartilage (not shown), the lateral cartilage (not shown), and the tissues and skin attached thereto.

The head 2 also includes cheeks 7. What is meant herein by the term "cheeks" is the area of the head including the anatomical structures known as the zygomatic bone (not shown), the maxillary bone (not shown), and the tissues and skin attached thereto.

The nasal strip 10 is adhesively affixed to the bridge 6, the nasal walls 8,9, and the cheeks 7. As shall be described in detail below, the structure of the nasal strip 10, when affixed to the head 2, allows the nasal walls 8,9 to be gently pulled outwardly in the general directions of arrows 13,15, respectively, thereby enhancing the passage of air through the nasal passages 3.

Referring now to FIG. 3, there is shown an elevational view of the nasal strip 10 prior to attachment to the head 2. A first section 10a of the nasal strip 10 spans the bridge 6 of the nose 4, and is attached thereto. A second section 10b of the nasal strip 10 adhesively affixes to the nasal wall 8. Similarly, a third section 10c of the nasal strip 10 adhesively affixes to the nasal wall 9. Moreover, a pair of end sections 10d of the nasal strip 10 adhesively affixes to the cheeks 7.

The overall length of the nasal strip 10 is represented by a distance $D_1$ in FIG. 3. The width of the portion of the nasal strip 10 which contacts the nose, i.e. the sections 10a, 10b, and 10c, is represented by a distance $D_3$. Moreover, the length of the portion of the nasal strip 10 which contacts the nose 4, i.e. the sum of the sections 10a, 10b, and 10c, is represented by a distance $D_2$. Preferably, the magnitudes of the distances are as follows: $D_1$=12.0 cm., $D_2$=7.2 cm., and $D_3$=1.5 cm.

Figure 4:
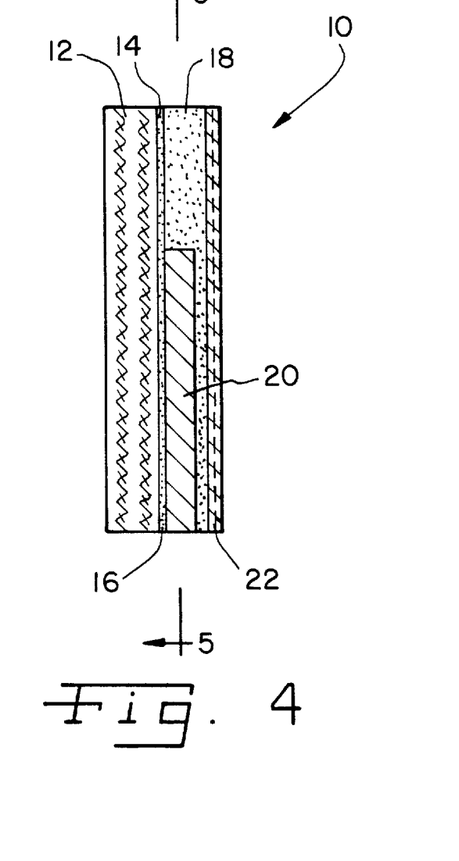
FIG. 4 is an enlarged cross sectional view taken along the lines 4—4 of FIG. 3 as viewed in the direction of the arrows.
Figure 5:
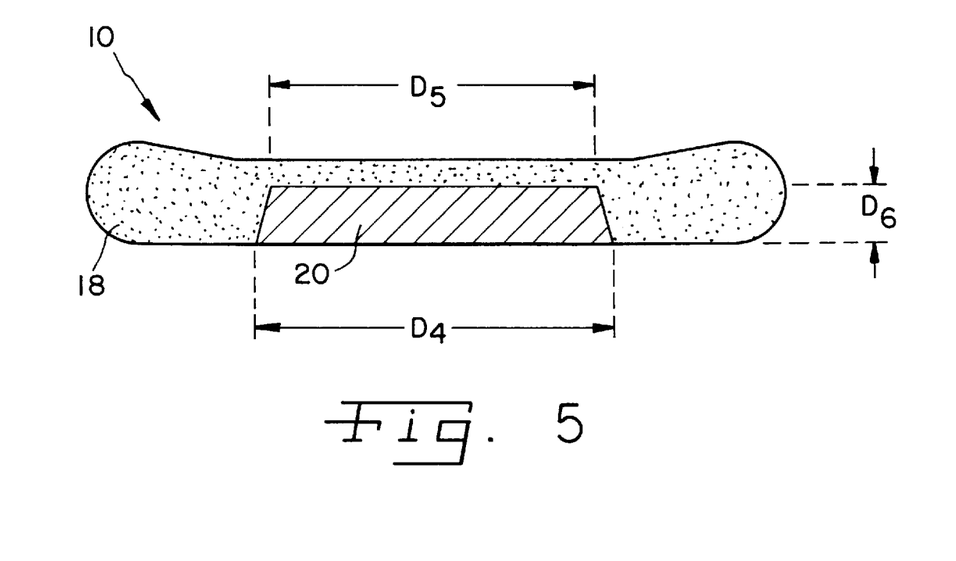
FIG. 5 is a cross sectional view taken along the lines 5—5 of FIG. 4 as viewed in the direction of the arrows.

Referring now to FIGS. 4 and 5, there is shown the nasal strip 10. FIG. 4 is a cross-sectional view taken along the lines 4—4 of FIG. 3, whereas FIG. 5 is a cross-sectional view taken along the lines 5—5 of FIG. 4.

The nasal strip 10 includes a base 12 made of a ventilated material. In general, the vented material may be a perforated film of polymeric material, woven nylon, or other similar fibers. In particular, one material which may be used is Non-Woven Material #1766 commercially available from 3M Corporation.

The sections 10a, 10b, and 10c of the base 12 are shown as white in color. However, as shown in FIGS. 1 and 3, the end sections 10d of the base 12 are colored in a non-reflective black or "burned cork" finish to reduce the amount of glare generated off of the cheeks 7 when the cheeks 7 are subjected to bright light. This feature is particularly useful when the nasal strip 10 is being used by an athlete on a bright, sunny day or under the lights of a lit playing surface.

The base 12 includes a surface 14 as shown in FIG. 4. The surface 14 of the base 12 has a layer of adhesive 16 disposed thereon that facilitates the attachment of a biasing member 20 to the base 12. For example, an acrylic based adhesive may be used as the adhesive 16. When the nasal strip 10 is affixed to the head 2, the biasing member 20 exerts biasing forces on the nasal walls 8,9 in the general directions of the arrows 13,15 of FIGS. 1 and 2A. These biasing forces hold the nasal walls 8,9 open, thereby allowing the nasal passages 3 to be more fully opened. The magnitude of the biasing forces created by the biasing member 20 can be altered by modifying the size thereof. Moreover, the nasal strip 10 may include a plurality of biasing members 20 to provide varying degrees of rigidity to the nasal strip.

Figure 5A:
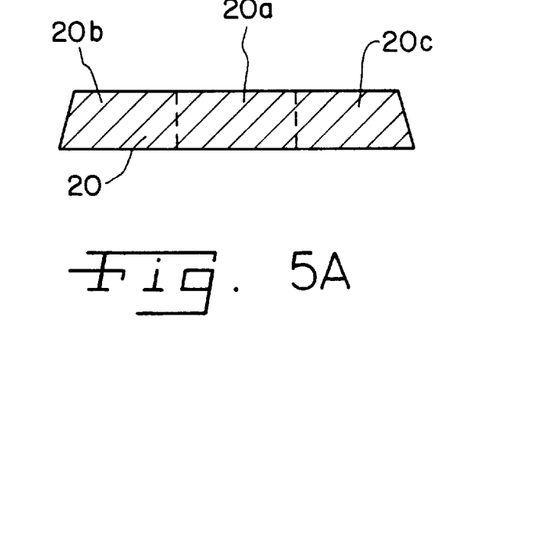
FIG. 5A is a cross sectional view of a biasing member of the nasal strip of FIG. 5.

Referring now to FIG. 5A, there is shown a cross sectional view of the biasing member 20 of FIG. 5. The biasing member includes an intermediate portion 20a, a first nasal wall support portion 20b, and a second nasal wall support portion 20c. The intermediate portion 20a spans the bridge 6 of the nose 4. The first nasal wall support portion 20b of the biasing member 20 exerts biasing forces on the nasal wall 8. Similarly, the second nasal wall support portion 20c of the biasing member 20 exerts biasing forces on the nasal wall 9.

The biasing member 20 is made of an aluminum alloy. Preferably, the biasing member 20 is made of 1100 low copper, high purity aluminum alloy. The use of an aluminum alloy as described herein provides the rigidity needed to ensure that the nasal strip 10 can open the nasal passages 3 of the nose 4 more fully. At the same time, the use of an aluminum alloy as described herein provides the flexibility necessary to conform to the particular anatomy of a user's nose.

In order to better conform to the anatomy of the nose 4, the biasing member 20 is provided in a trapezoidal shape. The length of the lower edge of the biasing member 20 is represented by a distance $D_4$ in FIG. 5, whereas the length of the upper edge of the biasing member 20 is represented by a distance $D_5$. Moreover, the width of the biasing member 20 is represented by a distance $D_6$. Preferably, the magnitudes of the distances are as follows: $D_4$=6.2 cm., $D_5$=5.7 cm., and $D_6$=1.0 cm.

Referring again to FIGS. 4 and 5, disposed on the adhesive 16 is a facial adhesive 18. The facial adhesive 18 envelops the biasing member 20, and affixes the nasal strip 10 to the head 2. The facial adhesive 18 may be an unsupported acrylic adhesive which adequately holds the nasal strip 10 to the head 2 without requiring excessive forces to remove the nasal strip 10 from the head of the user when the user desires to remove nasal strip 10. In particular, the facial adhesive 18 must be strong enough to adhere to the head 2 in the presence of the biasing forces created by the biasing member 20, yet the facial adhesive must not create discomfort or pain upon removal of the nasal strip 10 from the head 2.

The facial adhesive 18 has a strippable liner 22 positioned over and in contact therewith. The facial adhesive 18 is interposed between the adhesive 16 and the strippable liner 22, thereby protecting the facial adhesive 18 until use. The strippable liner 22 may be made of a silicone impregnated paper.

The nasal strip 10 is relatively simple to manufacture. The base 12 is commercially available, e.g. from 3M Corporation as described above, with the adhesive 16 already attached thereto. The base 12/adhesive 16 composite can be purchased in either rectangular, precut strips or on a roll. The biasing member 20, also available in either precut strips or on a roll, is subsequently affixed to the adhesive 16. The base 12, the adhesive 16, and the biasing member 20 create a first sub-assembly. The facial adhesive 18 is applied to the strippable liner 22, likewise commercially available in precut strips or on a roll, in a known manner to create a second sub-assembly. Thereafter, the facial adhesive 18 of the second sub-assembly is adhesively affixed to the adhesive 16 and the biasing member 20 of the first sub-assembly to create the final assembly.

The final assembly can then be cut in a known die operation to create the outline as depicted in FIGS. 3 and 5. Thus, if a material would need to be changed, such as the type of alloy utilized in the biasing member 20, the process can be altered quickly and with minimal disruption. Likewise, if it were desirable to alter the outline of the nasal strip 10 for a particular design or application, such changes can be made simply by modifying or replacing the die.

Figure 6:
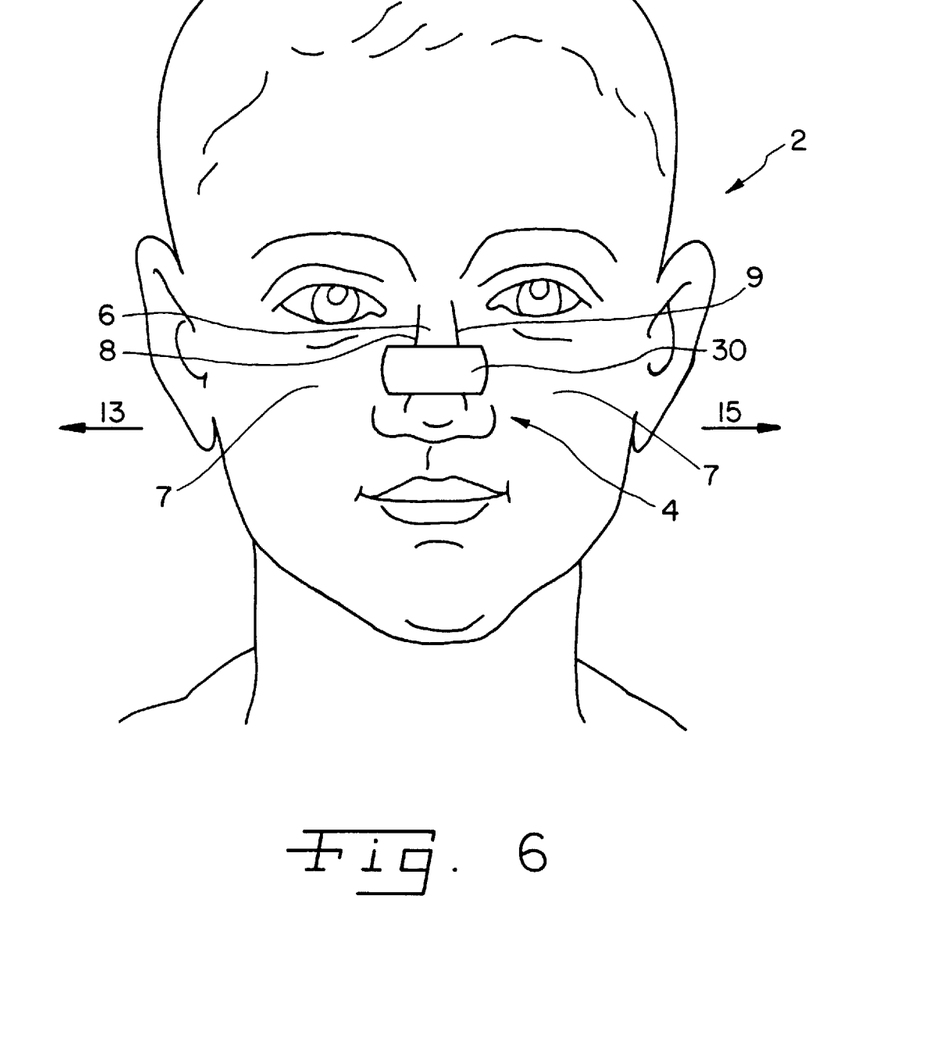
FIG. 6 is a front elevational view of a human head with a second embodiment of a nasal strip attached thereto which incorporates the features of the present invention therein.

Referring now to FIG. 6, there is shown the human head 2 with a second embodiment of a nasal strip 30 attached thereto. The nasal strip 30 is essentially the same as the nasal strip 10, except that the end sections 10d of the nasal strip 10 have been removed (see FIG. 3). The nasal strip 30 may be used in lieu of the nasal strip 10 when it is not necessary to utilize the glare reducing features of the end sections 10d of the nasal strip 10. More specifically, when the nasal strip is being used by someone other than an athlete on a bright, sunny day or under the lights of a lit playing surface, the nasal strip 30 may be used in lieu of the nasal strip 10.

In FIG. 6, the same reference numerals are used to designate the same components shown in FIGS. 1, 2, and 2A which were discussed above. Also, in FIGS. 8 and 9, the same reference numerals are used to designate the same components shown in FIGS. 4 and 5, which were discussed above.

The nasal strip 30 is adhesively affixed to the bridge 6 and the nasal walls 8,9, but does not extend to the cheeks 7. The structure of the nasal strip 30, when affixed to the head 2, allows the nasal walls 8,9 to be gently pulled outwardly in the general directions of arrows 13,15, respectively, thereby enhancing the passage of air through the nasal passages 3.

Figure 7:
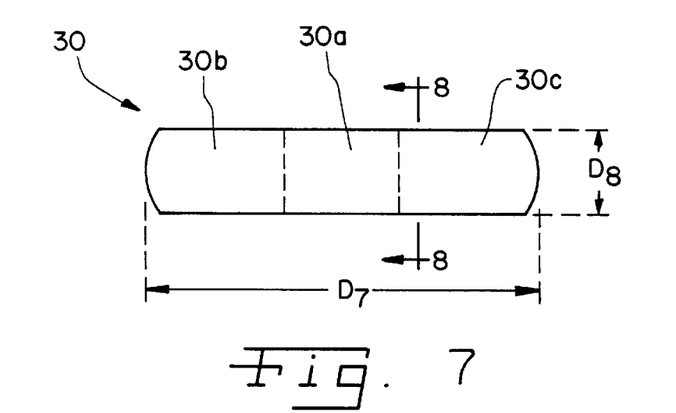
FIG. 7 is an elevational view of the nasal strip of FIG. 6 prior to attachment to the human head

Referring now to FIG. 7, there is shown an elevational view of the nasal strip 30. A first section 30a of the nasal strip 30 spans the bridge 6 of the nose 4, and is attached thereto. A second section 30b of the nasal strip 30 adhesively affixes to the nasal wall 8. Similarly, a third section 30c of the nasal strip 30 adhesively affixes to the nasal wall 9.

The overall length of the nasal strip 30 is represented by a distance $D_7$ in FIG. 7, whereas the overall width of the nasal strip 30 is represented by a distance $D_8$. Preferably, the magnitude of the distances are as follows: $D_7$=7.2 cm. and $D_8$=1.5 cm.

Figure 8:
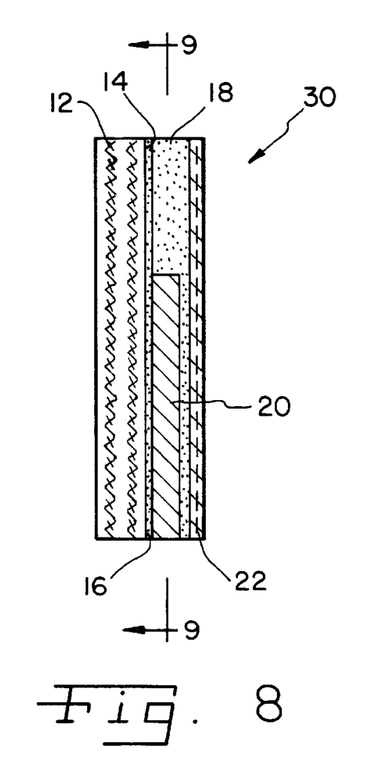
FIG. 8 is an enlarged cross sectional view taken along the line 8—8 of FIG. 7 as view in the direction of the arrows.
Figure 9:
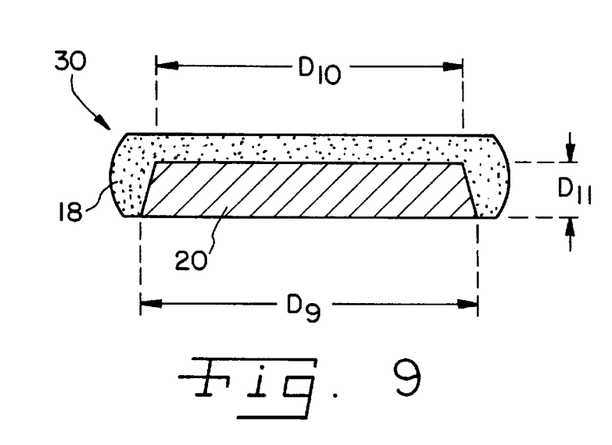
FIG. 9 is a cross sectional view taken along the lines 9—9 of FIG. 8 as viewed in the direction of the arrows.

Referring now to FIGS. 8 and 9, there is shown the nasal strip 30. FIG. 8 is a cross-sectional view taken along the lines 8—8 of FIG. 7, whereas FIG. 9 is a cross-sectional view taken along the lines 9—9 of FIG. 8.

As with the nasal strip 10 of FIG. 1, when the nasal strip 30 is adhesively affixed to the head 2, the biasing member 20 exerts biasing forces on the nasal walls 8,9 in the general directions of arrows 13,15, respectively, of FIG. 6. These biasing forces hold the nasal walls 8,9 open, thereby enhancing the passage of air through the nasal passages 3.

Moreover, the biasing member 20 is made of an aluminum alloy. Preferably, the biasing member 20 is made of 1100 low copper, high purity aluminum alloy. The use of an aluminum alloy as described herein provides the rigidity needed to ensure that the nasal strip 30 can open the nasal passages 3 of the nose 4 more fully. At the same time, the use of an aluminum alloy as described herein provides the flexibility necessary to conform to the particular anatomy of a user's nose.

In order to better conform to the anatomy of the nose 4, the biasing member 20 is provided in a trapezoidal shape. The length of the lower edge of the biasing member 20 is represented by a distance $D_9$ in FIG. 9, whereas the length of the upper edge of the biasing member 20 is represented by a distance $D_{10}$. Moreover, the width of the biasing member 20 is represented by a distance $D_{11}$. Preferably, the magnitudes of the distances are as follows: $D_9$=6.2 cm., $D_{10}$=5.7 cm., and $D_{11}$=1.0 cm.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

For example, the biasing member 20 is disclosed as being an aluminum alloy. The use of an aluminum alloy in the construction of the biasing member 20 in the present invention is particularly beneficial in that numerous advantages are achieved as described above. However, many of these advantages can be achieved by constructing the biasing member 20 from other metallic materials.

Also, the size and shape of the nasal strips 10,30 in relation to the head 2 are shown in FIGS. 1 and 6. However, it should be appreciated that the size and shape of the nasal strips 10,30 can be altered and still achieve many advantages of the present invention so long as the nasal strip 10 exerts biasing forces on the nasal walls 8,9 in the manner hereinbefore described.

What is claimed is:

1. An apparatus for opening nasal passages of a human head having a nose, a first cheek and a second cheek, with said nose having a bridge portion, a first nasal wall and a second nasal wall, comprising:

a metallic biasing member having a length sufficient to span a distance from said first nasal wall to said second nasal wall across said bridge portion;

a non-woven base, secured to said biasing member, having a length sufficient to span a distance from said first cheek to said second cheek across said nose;

an adhesive material disposed directly on said biasing member and said base for attaching said biasing member and said base to said human head; and a strippable liner positioned in contact with said adhesive material.

2. An apparatus for opening nasal passages of a human head having a nose, a first cheek and a second cheek, with said nose having a bridge portion, a first nasal wall and a second nasal wall, comprising:

a biasing member having a length sufficient to span a distance from said first nasal wall to said second nasal wall across said bridge portion;

a base, secured to said biasing member, having a length sufficient to span a distance from said first cheek to said second cheek across said nose, and an adhesive material for attaching said biasing member and said base to said human head, said adhesive material being disposed directly on said biasing member and said base.

3. The apparatus of claim 2, wherein:

said biasing member includes a first nasal wall support portion and a second nasal wall support portion;

said base includes a first end portion and a second portion;

said adhesive material is disposed directly on (1) said first nasal wall support portion of said biasing member, (2) said second nasal wall support portion of said biasing member, (3) said first end portion of said base, and (4) said second end portion of said base.

4. The apparatus of claim 2, wherein said biasing member includes a metallic material.

5. The apparatus of claim 4, wherein said metallic material is an aluminum alloy.

6. The apparatus of claim 2, wherein:

said base includes a first end portion and a second end portion, said first end portion and said second end portion each has a substantially black color.

7. The apparatus of claim 6, wherein:

said base further includes an intermediate portion which connects said first end portion and said second end portion, and said intermediate portion has a substantially white color.

8. The apparatus of claim 2, wherein:

said base includes a first end portion and a second end portion, said first end portion and said second end portion each has a first color, said base further includes an intermediate portion which connects said first end portion and said second end portion, and said intermediate portion has a second color which is different from said first color.

9. The apparatus of claim 8, wherein said first color is darker than said second color.

10. The apparatus of claim 2, wherein said base includes a non-woven material.

11. The apparatus of claim 2, wherein:

said base has a first side, said biasing member has a first side and a second side, said first side of said base is secured to said first side of said biasing member, and said adhesive material is disposed directly on said first side of said base and said second side of said biasing member.

12. The apparatus of claim 11, further comprising a strippable liner positioned in contact with said adhesive material.

13. The apparatus of claim 2, wherein said biasing member possesses a trapezoidal shape.

14. An apparatus for opening nasal passages of a human head having a nose, with said nose having a bridge portion, a first nasal wall, and a second nasal wall, comprising:

a metallic biasing member having a length sufficient to span a distance from said first nasal wall to said second nasal wall across said bridge portion, said biasing member further having a first nasal wall support portion and a second nasal wall support portion; and an adhesive material disposed directly on (1) said first nasal wall support portion of said biasing member, and (2) said second nasal wall support portion of said biasing member.

15. The apparatus of claim 14, wherein said biasing member further includes an intermediate portion which connects said first nasal wall support portion to said second nasal wall support portion.

16. The apparatus of claim 15, wherein when said apparatus is attached to said human head:

said adhesive material secures said first nasal wall support portion of said biasing member to said first nasal wall, said adhesive material secures said second nasal wall support portion of said biasing member to said second nasal wall, and said intermediate portion of said biasing member is juxtaposed to said bridge portion.

17. The apparatus of claim 14, wherein said metallic material is an aluminum alloy.

18. The apparatus of claim 14, further comprising a strippable liner which is positioned in contact with said adhesive material.

19. The apparatus of claim 14, further comprising a base secured to said biasing member.

20. The apparatus of claim 19, wherein said base includes a non-woven material.

21. The apparatus of claim 14, wherein said biasing member possesses a trapezoidal shape.

22. A method of opening nasal passages of a human head having a nose, a first cheek and a second cheek, with the nose having a bridge portion, a first nasal wall, and a second nasal wall, comprising:

providing a biasing member having a length sufficient to span a distance from the first nasal wall to the second nasal wall, providing a base having a length sufficient to span a distance from the first cheek to the second cheek across the nose; and attaching the biasing member and the base to the human head so that (1) the biasing member is juxtaposed to the first nasal wall, the second nasal wall, and the bridge portion, and (2) the base is juxtaposed to the first cheek, the second cheek and the nose.

23. The method of claim 22, wherein the biasing member includes a metallic material.

24. The method of claim 22, wherein (1) a first end portion of the base has a substantially black color, and (2) a second end portion of the base has a substantially black color, and further comprising the steps of:

positioning the first end portion of the base adjacent to the first cheek, and positioning the second end portion of the base adjacent to the second cheek.

25. The method of claim 24, wherein a third portion of the base has a substantially white color, and further comprising the step of:

positioning the third portion of the base adjacent to the nose.

26. The method of claim 22, wherein (1) a first end portion of the base possesses a first color, (2) a second end portion of the base possesses the first color, and (3) and a third portion of the base possesses a second color which is different from the first color, further comprising the steps of:

positioning the first end portion of the base adjacent to the first cheek, positioning the second end portion of the base adjacent to the second cheek; and positioning the third portion of the base adjacent to the nose.

27. The method of claim 26, wherein the first color is darker than the second color.

28. The method of claim 22, wherein the biasing member possesses a trapezoidal shape.

* * * * *